(12) United States Patent
Bar-Tal et al.

(10) Patent No.: US 10,441,236 B2
(45) Date of Patent: Oct. 15, 2019

(54) INTEGRATION BETWEEN 3D MAPS AND FLUOROSCOPIC IMAGES

(71) Applicant: BIOSENSE WEBSTER (ISRAEL) LTD., Yokneam (IL)

(72) Inventors: Meir Bar-Tal, Haifa (IL); Tamir Demri, Gilon (IL); Tal Haim Bar-on, Kiryat Tivon (IL); Eliahu Zino, Atlit (IL); Ran Glazer, Haifa (IL); Gil Zigelman, Haifa (IL); Dror Berman, Haifa (IL)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 175 days.

(21) Appl. No.: 14/045,246

(22) Filed: Oct. 3, 2013

(65) Prior Publication Data
US 2014/0114173 A1 Apr. 24, 2014

Related U.S. Application Data (60) Provisional application No. 61/715,935, filed on Oct. 19, 2012.

(51) Int. Cl.
*A61B 5/00* (2006.01)
*A61B 6/00* (2006.01)
(Continued)

(52) U.S. Cl.
CPC .......... *A61B 6/5247* (2013.01); *A61B 5/0035* (2013.01); *A61B 5/0522* (2013.01);
(Continued)

(58) Field of Classification Search
CPC combination set(s) only.
See application file for complete search history.

(56) References Cited

U.S. PATENT DOCUMENTS 5,442,674 A * 8/1995 Picard ................. A61B 6/583
378/18
5,577,502 A 11/1996 Darrow et al.
(Continued)

FOREIGN PATENT DOCUMENTS

CN 101084840 A 12/2007
DE 102008058497 B3 12/2009
(Continued)

OTHER PUBLICATIONS

European Search Report dated Jul. 7, 2014 for corresponding Application No. EP13189397.
(Continued)

*Primary Examiner* — Joel Lamprecht
(74) *Attorney, Agent, or Firm* — Notaro, Michalos & Zaccaria P.C.

(57) ABSTRACT

A coordinate system registration module, including radiopaque elements arranged in a fixed predetermined pattern and configured, in response to the radiopaque elements generating a fluoroscopic image, to define a position of the module in a fluoroscopic coordinate system of reference. The module further includes one or more connections configured to fixedly connect the module to a magnetic field transmission pad at a predetermined location and orientation with respect to the pad, so as to characterize the position of the registration module in a magnetic coordinate system of reference defined by the magnetic field transmission pad.

15 Claims, 8 Drawing Sheets

(51) Int. Cl.
  *A61B 5/05* (2006.01)
  *A61B 5/06* (2006.01)
  *A61B 6/02* (2006.01)
  *A61M 25/01* (2006.01)
  *A61B 90/00* (2016.01)
  *A61B 34/20* (2016.01)

(52) U.S. Cl.
  CPC ............ *A61B 5/062* (2013.01); *A61B 5/7425* (2013.01); *A61B 6/02* (2013.01); *A61B 6/4417* (2013.01); *A61B 6/4441* (2013.01); *A61B 6/463* (2013.01); *A61B 6/485* (2013.01); *A61B 6/54* (2013.01); *A61B 90/37* (2016.02); *A61M 25/0108* (2013.01); *A61M 25/0127* (2013.01); *A61B 2034/2051* (2016.02); *A61B 2090/364* (2016.02); *A61B 2090/376* (2016.02); *A61B 2090/3954* (2016.02); *A61B 2090/3966* (2016.02)

(56) References Cited

U.S. PATENT DOCUMENTS

| | | | |
|---|---|---|---|
| 5,640,970 A * | 6/1997 | Arenas | 600/585 |
| 5,846,199 A * | 12/1998 | Hijlkema et al. | 600/435 |
| 6,285,902 B1 | 9/2001 | Kienzle, III et al. | |
| 6,314,310 B1 | 11/2001 | Ben-Haim | |
| 6,324,310 B1 | 11/2001 | Brownlee | |
| 6,325,758 B1 * | 12/2001 | Carol | A61N 5/1049 128/916 |
| 6,374,134 B1 | 4/2002 | Bladen et al. | |
| 6,400,981 B1 | 6/2002 | Govari | |
| 6,484,049 B1 * | 11/2002 | Seeley et al. | 600/426 |
| 6,558,333 B2 | 5/2003 | Gilboa et al. | |
| 6,652,579 B1 * | 11/2003 | Cox et al. | 623/1.34 |
| 6,711,429 B1 | 3/2004 | Gilboa et al. | |
| 7,174,202 B2 | 2/2007 | Bladen et al. | |
| 7,386,339 B2 | 6/2008 | Strommer et al. | |
| 8,208,988 B2 | 6/2012 | Jensen | |
| 9,038,260 B2 * | 5/2015 | Wu | 29/458 |
| 2002/0041655 A1 * | 4/2002 | Mitschke | A61B 6/547 378/207 |
| 2003/0040879 A1 * | 2/2003 | Jutras | A61B 90/10 702/94 |
| 2003/0059097 A1 | 3/2003 | Abovitz et al. | |
| 2004/0013240 A1 | 1/2004 | Mitschke | |
| 2004/0199072 A1 | 10/2004 | Sprouse et al. | |
| 2005/0053200 A1 | 3/2005 | Sukovic et al. | |
| 2005/0245807 A1 * | 11/2005 | Boese | A61B 5/1127 600/407 |
| 2007/0073137 A1 * | 3/2007 | Schoenefeld | A61B 90/36 600/407 |
| 2007/0122020 A1 * | 5/2007 | Claus | A61B 6/583 382/131 |
| 2008/0002871 A1 | 1/2008 | Gunzert-Marx et al. | |
| 2008/0114238 A1 | 5/2008 | Llyod | |
| 2008/0114267 A1 | 5/2008 | Llyod et al. | |
| 2008/0119712 A1 | 5/2008 | Lloyd | |
| 2008/0154120 A1 | 6/2008 | von Jako et al. | |
| 2008/0183071 A1 | 7/2008 | Strommer et al. | |
| 2008/0300478 A1 | 12/2008 | Zuhars et al. | |
| 2009/0213997 A1 | 8/2009 | Maschke | |
| 2010/0016712 A1 * | 1/2010 | Bartal | A61B 5/06 600/425 |
| 2010/0044573 A1 | 2/2010 | Yagi et al. | |
| 2010/0137707 A1 * | 6/2010 | Hunter et al. | 600/424 |
| 2010/0305427 A1 | 12/2010 | Huber et al. | |
| 2011/0015519 A1 * | 1/2011 | Graumann | A61B 6/583 600/424 |
| 2011/0054297 A1 | 3/2011 | Bulitta et al. | |
| 2011/0096899 A1 | 4/2011 | Masuo et al. | |
| 2011/0130521 A1 * | 6/2011 | Thatcher et al. | 525/415 |
| 2011/0282184 A1 | 11/2011 | Klingenbeck et al. | |
| 2012/0165656 A1 | 6/2012 | Montag et al. | |
| 2012/0201421 A1 | 8/2012 | Hartmann | |

FOREIGN PATENT DOCUMENTS

| | | |
|---|---|---|
| DE | 102009034671 | 1/2011 |
| EP | 1510182 | 3/2005 |
| EP | 1510182 A2 | 3/2005 |
| EP | 1510182 B1 | 1/2010 |
| JP | 2003299642 A | 10/2003 |
| JP | 2012130703 A | 7/2012 |
| WO | 2011029910 A1 | 3/2011 |
| WO | 2012090148 A1 | 7/2012 |
| WO | 2012127353 A1 | 9/2012 |
| WO | WO2012127353 | 9/2012 |
| WO | 2013028582 A1 | 2/2013 |

OTHER PUBLICATIONS

U.S. Appl. No. 61/715,935, filed Oct. 19, 2012.
International Search Report for EP15201537 filed May 25, 2106.
Japanese official action for corresponding Japanese patent application No. 2013-217073, dated Jul. 18, 2017.
Australian Examination Report for AU2013245533 filed May 8, 2014.
Chinese Office Action and Search Report for CN201310491716.1 filed Oct. 18, 2013.
European Search Report for EP17150588 filed Jun. 17, 2017.
Preliminary Opinion dated Aug. 13, 2018 in EP13189397.6.
Examination Report dated Apr. 3, 2019 in AU2018202088.
Wen, Ji, "Electromagnetic tracking for Medical Imaging" (2010) All Theses and Dissertations (ETDs). 469, https://openscholarship.wustl.edu/etd/469.
V. V. Kindratenko, "A survey of electromagnetic position tracker calibration techniques" Virtual Reality: Research, Development and Applications 5, 169-182 (2000).
Examination Report dated May 3, 2019 in EP17150588.6.

* cited by examiner

FIG. 8

INTEGRATION BETWEEN 3D MAPS AND FLUOROSCOPIC IMAGES

CROSS-REFERENCE TO RELATED APPLICATION

This application claims the benefit of U.S. Provisional Patent Application 61/715,935 filed 19 Oct. 2012, which is incorporated herein by reference.

FIELD OF THE INVENTION

The present invention relates generally to combining images, and specifically to combining a two-dimensional fluoroscope image with a three-dimensional map.

BACKGROUND OF THE INVENTION

In current cardiac catheterization systems, the operating physician must often observe two different images simultaneously, on two different screens: 2D fluoroscopic images of the thorax and 3D maps of the heart. Such 3D maps may be generated, for example, using magnetic tracking of the catheter tip in the heart. Both the fluoroscopic images and the 3D maps may show the catheter, but from different angles and perspectives. Because of the lack of automatic registration and coordination between the fluoroscopic and 3D views, the physician is required to switch his or her attention back and forth between the displays and mentally register the different information that they contain.

Various methods are known in the patent literature for automatically registering a fluoroscopic image with a 3D map. Such methods are described, for example, in U.S. Pat. No. 6,314,310, whose disclosure is incorporated herein by reference.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides a coordinate system registration module, including:

radiopaque elements arranged in a fixed predetermined pattern and configured, in response to the radiopaque elements generating a fluoroscopic image, to define a position of the module in a fluoroscopic coordinate system of reference; and one or more connections configured to fixedly connect the module to a magnetic field transmission pad at a predetermined location and orientation with respect to the pad, so as to characterize the position of the registration module in a magnetic coordinate system of reference defined by the magnetic field transmission pad.

In a disclosed embodiment, the module includes a pair of parallel plates defining a line of symmetry, and the radiopaque elements include a plurality of radiopaque markers distributed symmetrically about the line.

In an alternative disclosed embodiment, the module includes a pair of parallel plates defining a line of symmetry, and the radiopaque elements include a radiopaque predetermined two-dimensional shape centered on the line of symmetry and orthogonal thereto. Typically, the predetermined shape is selected from a group including a disk and a rectangle.

There is further provided, according to an embodiment of the present invention, a method for registering coordinate systems, including:

arranging radiopaque elements in a fixed predetermined pattern within a registration module;

generating a fluoroscopic image of the radiopaque elements;

evaluating a fluoroscopic position of the registration module in a fluoroscopic coordinate system of reference in response to the fluoroscopic image;

fixedly connecting the registration module to a magnetic field transmission pad at a predetermined location and orientation with respect to the pad, so as to characterize a magnetic position of the registration module in a magnetic coordinate system of reference defined by the magnetic field transmission pad; and registering the fluoroscopic coordinate system with the magnetic coordinate system by equating the fluoroscopic position of the registration module with the magnetic position of the registration module.

Typically, the module includes a pair of parallel plates defining a line of symmetry, and the radiopaque elements include a plurality of radiopaque markers distributed symmetrically about the line.

Alternatively or additionally, the module includes a pair of parallel plates defining a line of symmetry, and the radiopaque elements include a radiopaque predetermined two-dimensional shape centered on the line of symmetry and orthogonal thereto. The predetermined shape may be selected from a group including a disk and a rectangle.

In an alternative embodiment registering the coordinate systems includes generating a first transformation relating the fluoroscope coordinate system of reference to a registration module coordinate system of reference, and a second transformation relating the registration module coordinate system of reference to the magnetic coordinate system of reference, and generating a compound transformation consisting of a composition of the first and second transformations.

Typically, registering the coordinate systems includes updating the compound transformation, and updating the compound transformation includes, in response to a change in a registration of the coordinate systems, updating the first transformation while maintaining the second transformation unchanged.

In a further alternative embodiment the method includes:

positioning a calibration element having further radiopaque elements on a table irradiated by a fluoroscope producing the fluoroscopic image;

generating a further fluoroscopic image of the calibration element; and calibrating movements of the table in response to the further fluoroscopic image.

The calibration element may include a ruler disposed at a known angle to the table.

In a yet further alternative embodiment the method includes generating a three-dimensional map of an object in the magnetic coordinate system of reference, and generating a two-dimensional fluoroscopic image including the object in the fluoroscopic coordinate system of reference, and aligning and positioning the two-dimensional fluoroscopic image with respect to the three-dimensional map in response to registering the fluoroscopic coordinate system with the magnetic coordinate system.

Typically, generating the three-dimensional map of the object includes generating the map in a first orientation of the object, and generating the two-dimensional fluoroscopic image in a second orientation of the object, and wherein aligning and positioning the two-dimensional fluoroscopic image with respect to the three-dimensional map includes altering one of the map and the image so that the map and the image align.

There is further provided, according to an embodiment of the present invention, a coordinate system calibration jig, including:

radiopaque elements arranged in a fixed predetermined pattern and configured, in response to the radiopaque elements generating a fluoroscopic image, to define a position of the jig in a fluoroscopic coordinate system of reference; and one or more connectors configured to receive magnetic sensors in respective predetermined fixed locations and orientations with respect to the jig, so that signals from the magnetic sensors in response to a magnetic field traversing the sensors characterize the position of the jig in a magnetic coordinate system of reference defined by the magnetic field.

The predetermined pattern may include a helix having a varying period length.

Alternatively or additionally, the predetermined pattern may include a helix having different numbers of elements within each period of the helix.

There is further provided, according to an embodiment of the present invention, a method, including:

arranging radiopaque elements in a fixed predetermined pattern;

defining, in response to the radiopaque elements generating a fluoroscopic image, a position of the jig in a fluoroscopic coordinate system of reference; and configuring one or more connectors to receive magnetic sensors in respective predetermined fixed locations and orientations with respect to the jig, so that signals from the magnetic sensors in response to a magnetic field traversing the sensors characterize the position of the jig in a magnetic coordinate system of reference defined by the magnetic field.

The present disclosure will be more fully understood from the following detailed description of the embodiments thereof, taken together with the drawings, in which:

DETAILED DESCRIPTION OF EMBODIMENTS

In the following description, like elements in the drawings are identified by like numerals, and the like elements are differentiated as necessary by appending a letter to the identifying numeral.

Figure 1:
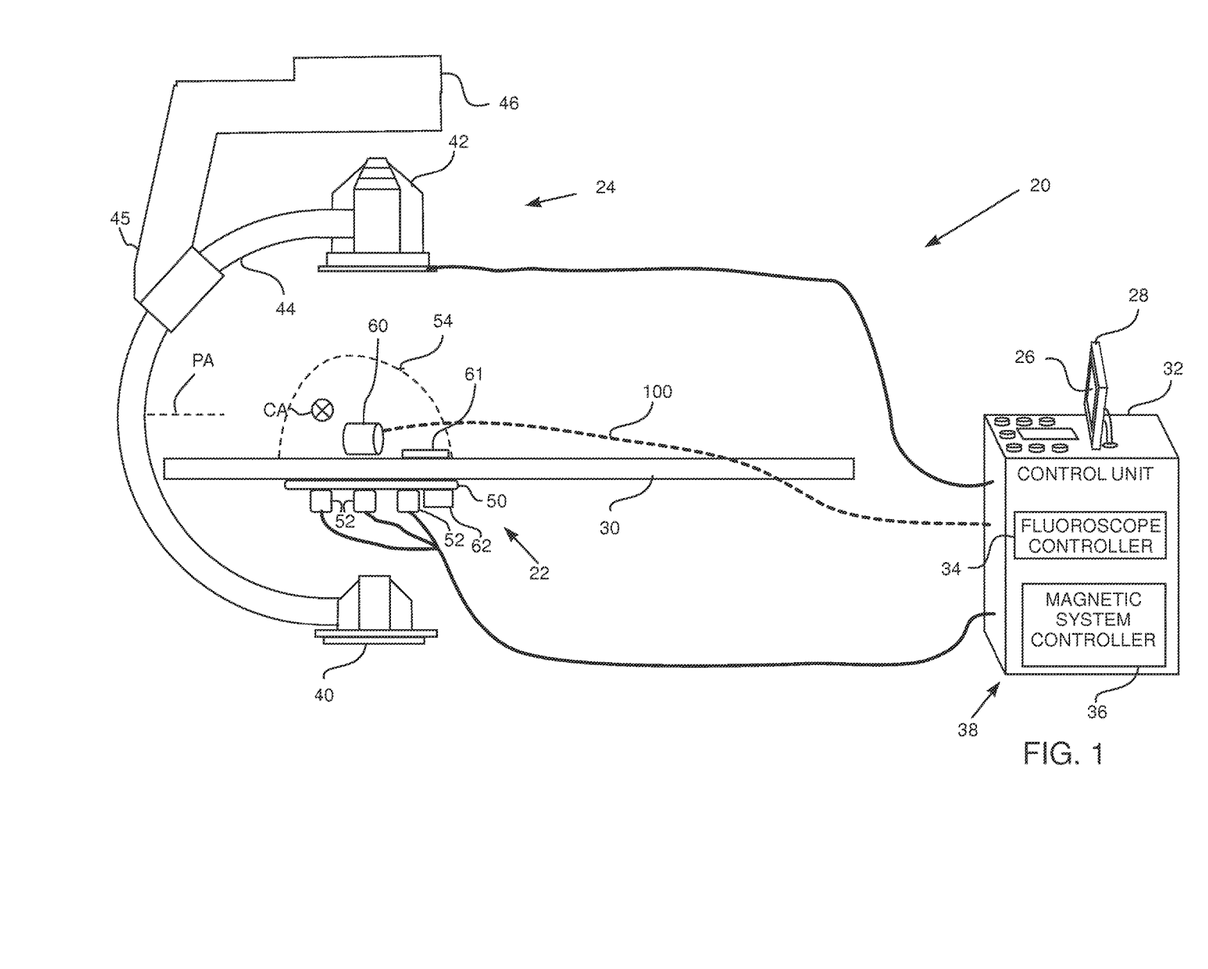
FIG. 1 is a schematic diagram illustrating a fluoroscopic image and magnetic mapping integration system in a calibration phase, according to an embodiment of the present invention.

FIG. 1 is a schematic diagram illustrating a fluoroscopic image and magnetic mapping integration system 20 in a calibration phase, according to an embodiment of the present invention. System 20 combines a three-dimensional (3D) map of a body organ that is acquired by a magnetic tracking system 22, with a two-dimensional (2D) fluoroscopic image of the patient acquired by a fluoroscope 24, so forming a combined display 26 that is presented to an operator of system 20 on a screen 28. In the calibration phase for system 20 illustrated in FIG. 1 the patient is not present. In a subsequent operational phase of system 20, illustrated in FIG. 5, the patient is assumed to be lying on a table 30 of system 20, and magnetic tracking system 22 and fluoroscope 24 acquire the 3D map and 2D image of the patient, as described in more detail below. Typically the 2D image acquired by the fluoroscope is of the chest of the patient, and the body organ mapped by the magnetic tracking system comprises the heart of the patient.

While in practice system 22 and system 24 may typically be configured as separate physical units with separate control units, in the present description, for simplicity, system 20 is assumed to be operated by a single control unit 32.

Control unit 32 comprises a fluoroscope controller 34 operating the fluoroscope, and a magnetic system controller 36 operating the magnetic tracking system, and the unit is under overall control of a system processor 38, the processor, inter alia, generating combined display 26 on screen 28. Software for processor 38 may be downloaded to the processor in electronic form, over a network, for example, or it may, alternatively or additionally, be provided and/or stored on non-transitory tangible computer-readable media, such as magnetic, optical, or electronic memory.

Fluoroscope 24 comprises an X-ray source 40 and a detector 42, the radiator and detector being mounted on opposite ends of a C-arm 44, assumed herein to comprise an arc of a circle. C-arm 44 is typically held at a lower end 45 of an L-arm 46, the L-arm being attached at its upper end to a ceiling of an operating theater, or at its lower end to the operating theater floor. C-arm 44 may be rotated around a horizontal pivot axis PA, which in the diagram is in the plane of the paper. C-arm 44 may also rotate around a C-arm axis CA, which is perpendicular to the plane of the paper and which passes through the center of the C-arm circle. Nominally, the two axes intersect at the C-arm center of rotation, also termed the iso-center, and are orthogonal to each other. The operator of system 20 is able to adjust rotations of fluoroscope 24 about axes PA and CA, as well as other geometrical parameters of the fluoroscope, using fluoroscope controller 34. (As described in more detail below, the calibration phase provides adjustments to nominal properties of fluoroscope 24, such as the ones exemplified above.)

Magnetic tracking system 22 comprises a location pad 50, which typically has three sets 52 of generally similar coils fixedly mounted on the pad. Each set 52 of coils typically comprises three orthogonally oriented coils, so that there are a total of nine coils fixedly attached to pad 50. Pad 50 is fixedly attached to the underside of table 30, and the coils, under control of magnetic system controller 36, transmit alternating magnetic fields into a region 54 in proximity to the pad and above the bed. In order to track an entity in region 54, herein assumed to comprise a catheter, one or more coils are attached to the catheter.

The one or more catheter coils generate signals in response to the magnetic fields received by the coils, and controller 36 acquires the signals from the coils, and processes the signals in order to determine a position of the catheter coils with respect to location pad 50. A system similar to magnetic tracking system 22 is the Carto™ system produced by Biosense Webster Inc., of Diamond Bar, Calif. In addition to tracking objects, such as catheters, magnetic tracking system 22 may be used to generate the 3D map of the body organ, or of a parameter related to the body organ. For example, system 22 may generate a 3D map of electropotentials on the surface of the heart of the patient, as is described for example, in U.S. Pat. No. 6,400,981 to Govari, which is incorporated herein by reference.

In order to register the coordinate systems, or frames of reference, of magnetic tracking system 22 and fluoroscope system 24, system 20, in its calibration phase, uses one or more registration elements. A given registration element has the property that its location and orientation may be determined simultaneously in both coordinate systems. Embodiments of the present invention use as a first registration element a helix calibration jig 60, and as a second registration element a location pad registration module 62. Helix calibration jig 60, also referred to herein as jig 60, is described in more detail with reference to FIG. 2. Registration module 62 is described in more detail with reference to FIG. 3.

In addition to the magnetic tracking coordinate system and the fluoroscope coordinate system, referred to above, a coordinate system based on location pad 50, and one based on registration module 62, are present in system 20. These systems, as is described in more detail below, are used as intermediaries in the registration of the magnetic tracking and the fluoroscope coordinate systems.

Figure 2:
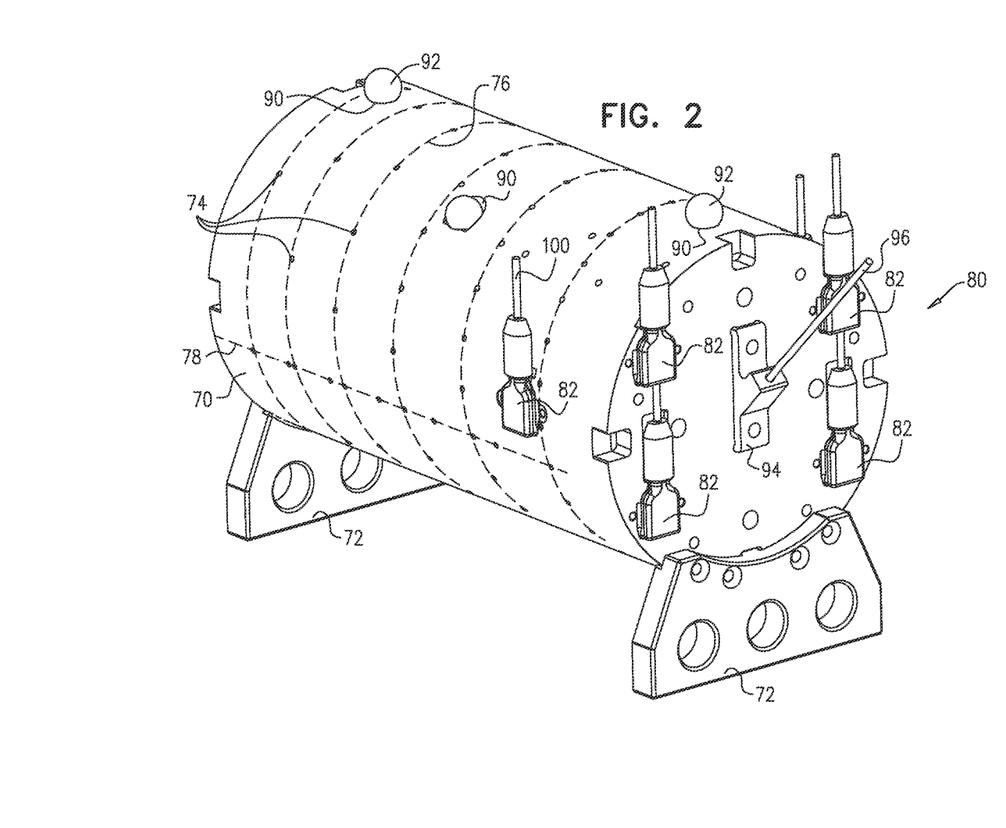
FIG. 2 is a schematic perspective diagram of a helix calibration jig used in the calibration phase, according to an embodiment of the present invention.

FIG. 2 is a schematic perspective diagram of helix calibration jig 60, according to an embodiment of the present invention. As will be apparent from the following description, jig 60 is "visible" in the fluoroscope system, to an extent that its position therein can be determined; in addition, the jig is trackable in the magnetic system so that its position in the magnetic tracking system is known. Jig 60 is formed as a plastic cylinder 70 which may be placed, using attached supports 72, on table 30, so that the axis of the cylinder is parallel to the table. Cylinder 70 has metal spheres 74 embedded in the cylinder. Metal spheres 74 provide good contrast fluoroscopic images of the spheres in jig 60 at detector 42. Spheres 74 are arranged in a helical pattern 76 within the cylinder, the helical pattern being configured to have a varying period length. In addition, within each period there is a different number of spheres. The helical pattern is illustrated by broken lines connecting spheres 74 of the helix.

In a disclosed embodiment of the present invention cylinder 70 has an approximate diameter of 120 mm, and an overall length of helical pattern 76 is approximately 200 mm. In the disclosed embodiment spheres 74 are arranged to define six periods, and Table I below gives exemplary lengths of each period in a direction parallel to an axis of cylinder 70, as well as exemplary numbers of spheres 74 within each period. Typically, spheres 74 are distributed evenly within each period.

TABLE I

| Helix period length [mm] | Number of spheres 72 in the period |
| --- | --- |
| 20 | 7 |
| 25 | 11 |
| 30 | 15 |
| 35 | 19 |
| 40 | 23 |
| 45 | 27 |

Further spheres 74 may be added to those of helical pattern 76. For example, more spheres 74 have been added to form straight lines 78 and 80 of spheres, line 78 corresponding to terminations of the helical periods, line 80 corresponding to the mid-points of the periods.

The different lengths of the helical pattern periods, together with the different numbers of spheres 74 in each period, enable fluoroscope controller 34 to uniquely identify each sphere 74. Adding further spheres to the helical pattern, as described above, further facilitates controller 34 in identifying spheres 74. The identification of spheres 74 is used in registering the magnetic system with the fluoroscope, as described below.

In some embodiments cylinder 70 comprises retro-reflectors 90 wherein removable balls 92 may be positioned. Typically the retro-reflectors are arranged symmetrically in cylinder 70, in a plane parallel to table 30 and may be used, with the aid of a laser for tracking the position of jig 60 on table 30. In an alternative embodiment, other metal spheres, generally similar to spheres 74, may be added to jig 60 to further aid in its positioning.

In addition to having metal spheres 74 embedded in cylinder 70, the cylinder is also configured to be able to have a number of magnetic sensors 82 fixedly attached, at known locations and with known orientations, to the cylinder. By way of example, there are six sensors 82 which may be attached to cylinder 70. Each sensor 82 typically comprises a set of three orthogonal coils, so that each sensor 82 is generally similar to a set 52 of coils in location pad 50. However, in other embodiments sensor 82 comprises fewer than three coils, and/or may comprise a magnetic detector such as a Hall detector, rather than coils.

Cylinder 70 also comprises a catheter holder 94. Holder 94 enables a catheter 96, having a magnetic sensor similar to sensor 82, to be fixedly positioned at a predefined location and with a predefined orientation with respect to cylinder 70. Connections from the sensor of the catheter, to magnetic system controller 36 are routed through the catheter. Connections 100 from sensors 82 are also coupled to the magnetic system controller, as is illustrated in FIG. 1.

Figure 3:
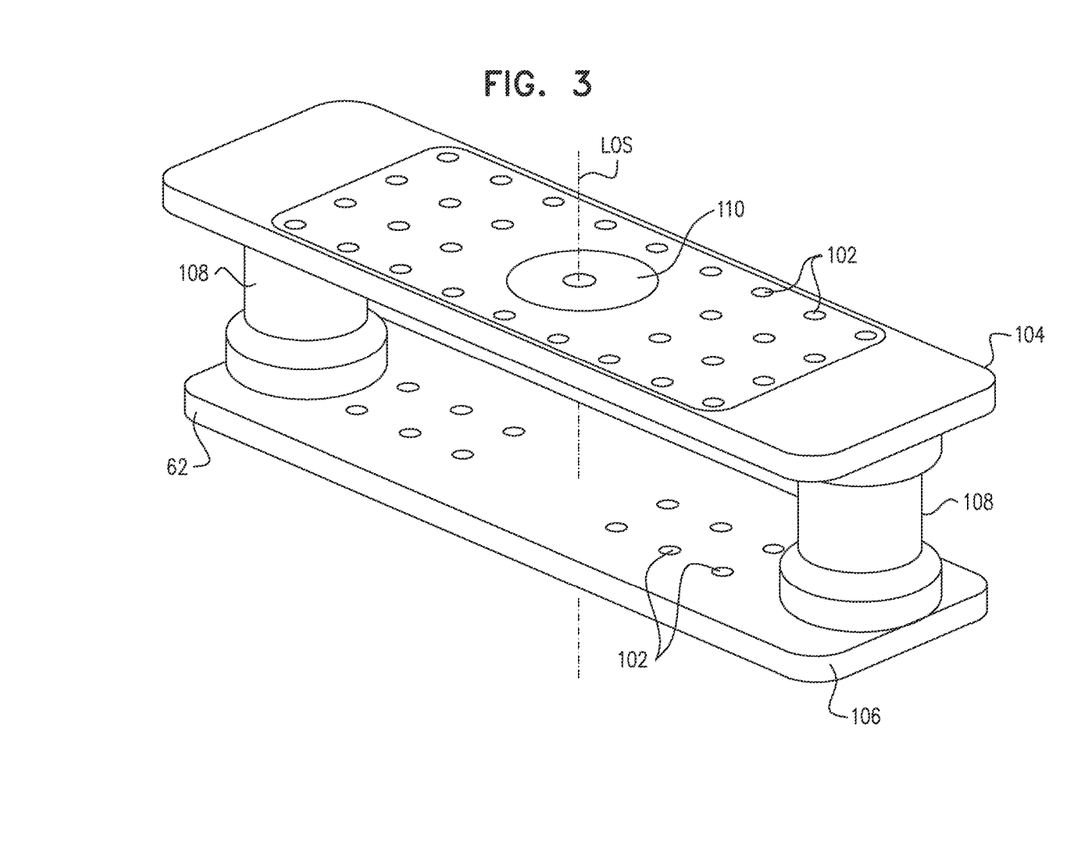
FIG. 3 is a schematic perspective diagram of a registration module, according to an embodiment of the present invention.

FIG. 3 is a schematic perspective diagram of registration module 62, according to an embodiment of the present invention. In contrast to jig 60, module 62 does not have magnetic sensors, and so is not trackable in the magnetic tracking system, and the position of the module with respect to location pad 50 cannot be determined by magnetic measurements. Rather, module 62 is configured to be fixedly connected in a known location and orientation with respect to the location pad. The fixed connection is typically accomplished by bolting the module, having predetermined mechanical measurements, to location pad 50. The fixed connection of module 62 to location pad 50 enables the location and orientation of the module in the magnetic tracking system to be known.

As for jig 60, module 62 comprises radiopaque markers 102, similar to spheres 74, which are incorporated in pre-defined patterns into two radio-transparent plates 104 and 106. Plates 104 and 106 are parallel to each other and are separated by a fixed distance defined by connectors 108 joining the two plates. In a disclosed embodiment the markers are distributed symmetrically about a line of symmetry LOS defined by the plates. Bolts (not shown) for connecting the module to the location pad may traverse connectors 108. In addition to markers 102, module 62 comprises a radiopaque disk 110 embedded into plate 104. In the disclosed embodiment, a center of disk 110 lies on the line of symmetry LOS, and the disk is oriented orthogonally to the line. Typically the location of disk 110, and the distortion of its shape (from round to elliptical) in a fluoroscopic image acquired by detector 42 enables fluoroscope controller 34 to accurately determine the location and orientation of the module in the fluoroscope system. An advantage of the design of module 62 is that the fluoroscopic image can accurately determine the location and orientation of the module even when not all markers 102 are visible in the fluoroscopic image. In an alternative embodiment disk 110 may be replaced by any predetermined 2D shape, typically symmetrical, such as a rectangle.

In order to operate system 20, the system is calibrated without the presence of a patient on table 30. The processes involved in the calibration are described in the flowcharts of FIGS. 4 and 5 below.

Figure 4:
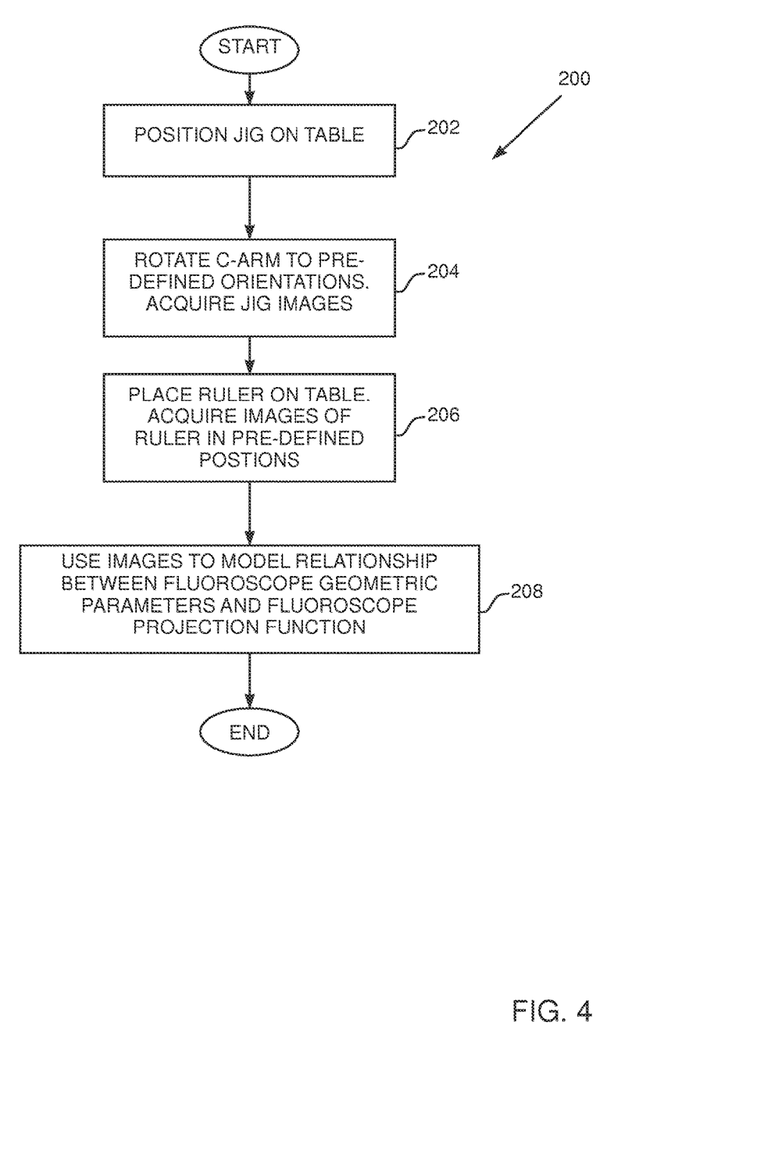
FIG. 4 is a flowchart of steps to model parameters of a fluoroscope system, according to an embodiment of the present invention.

FIG. 4 is a flowchart 200 of steps to model parameters of fluoroscope system 24, according to an embodiment of the present invention. The model generated by the flowchart provides a function that is able to predict the image acquired by detector 42 of an object in a known position in the fluoroscope coordinate system. The model may also generate an inverse function, i.e., one that may be able to predict the position of an object in the fluoroscope coordinate system from the object's image, as acquired by detector 42.

For clarity, in the following description the fluoroscope coordinate system is assumed to comprise a set of xyz orthogonal axes that are fixed to C-arm 44 and that are based on pivot axis PA and C-arm axis CA (FIG. 1). The orientations of the axes are assumed to be as follows:

A z-axis is orthogonal to the CA and PA axes;

An x-axis is parallel to the CA axis; and

A y-axis is orthogonal to the x and z axes.

An origin for the axes may be assumed to be the projection of the PA axis onto the CA axis in z-axis orientation, although any other convenient origin may be used.

It will be understood that the definition of the above set of axes for the fluoroscope coordinate system is by way of example, and that other sets of axes will be apparent to those having ordinary skill in the art. All such sets of axes are assumed to be comprised within the scope of the present invention.

The model provided by the flowchart calibrates for differences from nominal values of geometric parameters of the fluoroscope, as well as differences from nominal relationships between the parameters. Some examples of elements calibrated for in the model are provided in Table II:

TABLE II

Possible differences from nominal values of fluoroscope geometric parameters

Actual rotations of C-arm 44 about axis CA, and/or about axis PA, may be different from those assumed by fluoroscope controller 34.
The CA and PA axes may not be orthogonal, and/or may not intersect.
A distance from source 40 to detector 42 may be different from that assumed by controller 34.
A line from source 40 to the center of detector 42 may not pass through the center of rotation.

Geometric parameters other than those exemplified in Table II are calibrated for in the process of flowchart 200, and such parameters will be apparent to those having ordinary skill in the art.

In an initial step 202, with neither location pad 50 nor registration module 62 present, jig 60 is placed on table 30 so that it is approximately on a line between source 40 and detector 42. The placement may be checked by using retro-reflectors 90, and using an image acquired by the detector to confirm correct placement. In the initial step, jig 60 is in an arbitrary position with respect to the fluoroscope coordinate system axes described above.

In a C-arm calibration step 204, the C-arm is rotated about axes CA and PA, by the fluoroscope controller, to various pre-defined orientations. In each orientation detector 42 acquires an image of spheres 74 in jig 60. Fluoroscope controller 34 may also apply other pre-defined movements to the C-arm, or its components. For example, detector 42 may be rotated about an axis orthogonal to the plane of the detector. For each pre-defined orientation or movement, detector 42 acquires an image of jig 60.

In a table calibration step 206, jig 60 may be removed, and a calibration element 61 (FIG. 1), herein assumed to comprise a ruler, having radiopaque markings is placed on table 30. The ruler is oriented at a known angle to the table, typically approximately parallel or approximately orthogonal to a line of symmetry of the table, so that an image acquired by detector 42 comprises an image of the ruler. For a selected orientation of axes CA and PA, typically an orientation where the rotations about the axes are nominally zero, fluoroscope controller 34 moves table 30 by predefined translations and rotations. After each movement detector 42 acquires an image of the ruler. The predefined translations are typically parallel to a length of the table, at right angles to the length, and orthogonal to a plane of the table. The rotations may be rotations around axes defined by the translations.

The translations and orientations applied in steps 204 and 206 move jig 60 or the ruler within the fluoroscope coordinate system, from their initial arbitrary location and orientations. Since, during steps 204 and 206 jig 60 and the ruler do not move relative to table 30, it is only the translations and orientations of fluoroscope 24, which are known, which alter the position of the jig and the ruler within the fluoroscope coordinate system.

Consequently, in a final fluoroscope modeling step 208, controller 34 is able to use the images acquired in steps 204 and 206, together with the values of the respective fluoroscope translations and orientations that are known for each image, to model a relationship between a fluoroscope projection function and geometric parameters used in steps 204 and steps 206, i.e., the motions of the fluoroscope and the motions of the table. The model relationship enables a prediction to be made by fluoroscope controller 34, assuming that an object is in a given location and orientation in the fluoroscope coordinate system, of an image of the object on detector 42. The model also enables controller 34 to determine the location and orientation of an object imaged by detector 42 from the image acquired by the detector. The determination is used to perform registration between the fluoroscope coordinate system and a location pad coordinate system based on a registration image.

Consideration of steps 202-208 shows that the model relationship generated in step 208 does not use magnetic measurements. Furthermore, the model only relies on the invariance of the radiopaque elements in the jig and the ruler, and on the fact that neither the jig nor the ruler move on table 30 during the operations performed in the steps.

Figure 5:
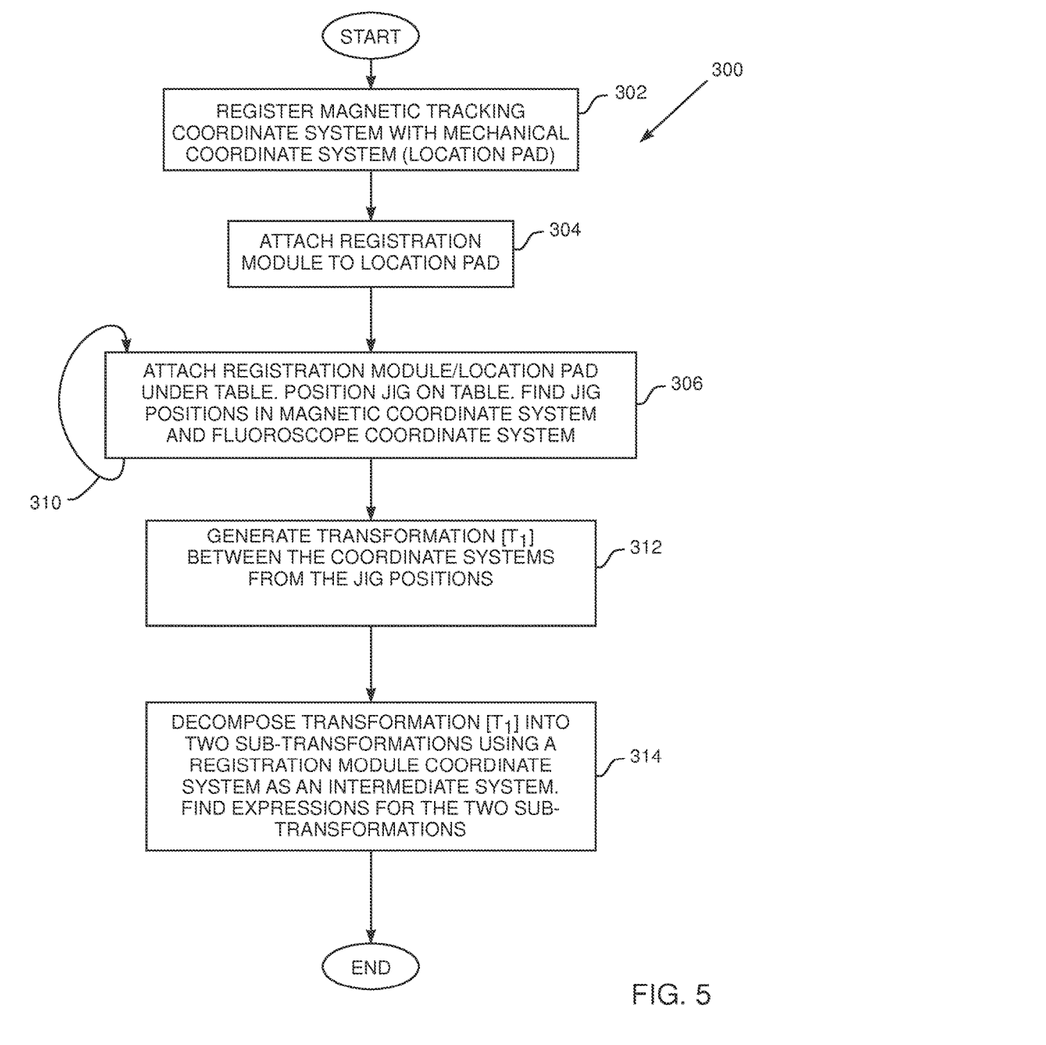
FIG. 5 is a flowchart of steps to register a magnetic tracking coordinate system with a fluoroscope coordinate system, according to an embodiment of the present invention.

FIG. 5 is a flowchart 300 of steps to register the magnetic tracking coordinate system with the fluoroscope coordinate system, according to an embodiment of the present invention. In the description of flowchart 300, it is assumed that flowchart 200 has already been performed, and that the model relationship has been generated.

In an initial step 302, the magnetic tracking coordinate system is registered with a mechanical coordinate system defined by the mechanical structure of location pad 50, herein termed the location pad coordinate system. The registration is typically performed prior to installation of the location pad into system 20, and may be performed on production of the location pad. The registration typically involves defining a location pad coordinate system in terms of the locations of the three sets 52 of coils comprising the location pad, measuring the location and orientation of a sensor coil, typically in a catheter, with respect to the location pad coordinate system, and relating signals from the sensor coil to the measured location and orientation. The registration performed in this step is a nominal registration, and corrections may be made to this nominal registration in later steps of the flowchart.

In a registration module attachment step 304, module 62 is physically attached to location pad 50, as described above. The physical attachment is typically performed prior to installation of the location pad and its attached registration module 62 into system 20. The physical attachment aligns the registration module into a predefined nominal location and orientation with respect to the location pad, so that a coordinate system based on the registration module, termed the registration module coordinate system, may be nominally registered with the location pad coordinate system. The nominal registration provided for in this step may also be corrected for in later steps of the flowchart.

In a registration step 306, the combined location pad and registration module is inserted, as a single unit, under table 30, and is fixedly attached to the table. In addition jig 60 is positioned on the table, above the registration module, and the table is moved so that the image acquired by detector 42 includes the images of the radiopaque elements of the registration module and of the jig.

Magnetic sensors 82 are fixed to jig 60, in their known locations and orientations, and the coils in the location pad are energized. Signals from the sensors, generated in response to the magnetic field radiated by the location pad coils, are received by magnetic system controller 36, and the controller analyzes the signals to determine a location and an orientation for the jig in the magnetic coordinate system.

Simultaneously, fluoroscope controller 34 analyzes the image acquired by detector 42 and, using the model generated in flowchart 200, determines a location and an orientation of jig 60 in the fluoroscope coordinate system.

Typically, as illustrated by an arrow 310, jig 60 is moved into other positions, by moving the jig on table 30, and/or by moving table 30. For each new position of the jig, locations and orientations of the jig in both coordinate systems are determined by controllers 34 and 36. The images acquired for the multiple jig positions of this step increase the accuracy of the transformation generated in the following step.

In a transformation generation step 312, system processor 38 receives the results of the locations and orientations of the jig in the two coordinate systems, in the multiple positions set in step 306. Processor 38 uses the results to generate a transformation $[T_1]$ between the two coordinate systems. Processor 38 may check the accuracy of transformation $[T_1]$, and adjust values of elements of the transformation, by using other magnetic sensors in known positions. For example, catheter 96 (with a magnetic sensor) may be inserted into holder 94 (FIG. 2), and the commonality of the catheter positions as measured in the two systems may be verified.

In a final step 314, processor 38 assumes that transformation $[T_1]$ is a composition of two sub-transformations, according to equation (1):

$$[T_{module,fluoro}]*[T_{magnetic,module}]=[T_1] \tag{1}$$

where $[T_{module,fluoro}]$ is a transformation between the fluoroscope coordinate system and a coordinate system defined by the registration module, and $[T_{magnetic,module}]$ is a transformation between the registration module coordinate system and the magnetic coordinate system.

The location and orientation of the registration module in the fluoroscope coordinate system are known from the images of the module acquired by detector 42, and these enable processor 38 to evaluate $[T_{module,fluoro}]$. While nominal location and orientation coordinates of the module in the magnetic coordinate system are known, (so that transformation $[T_{magnetic,module}]$ is nominally known) deviations from specification in the mounting of the registration module to the location pad cause deviations from the nominal values. Processor 38 consequently applies equation (1), where transformations $[T_1]$ and $[T_{module,fluoro}]$ are known, to find an actual expression for transformation $[T_{magnetic,module}]$. This expression is used in an operational phase of system 20, as is explained below.

Figure 6:
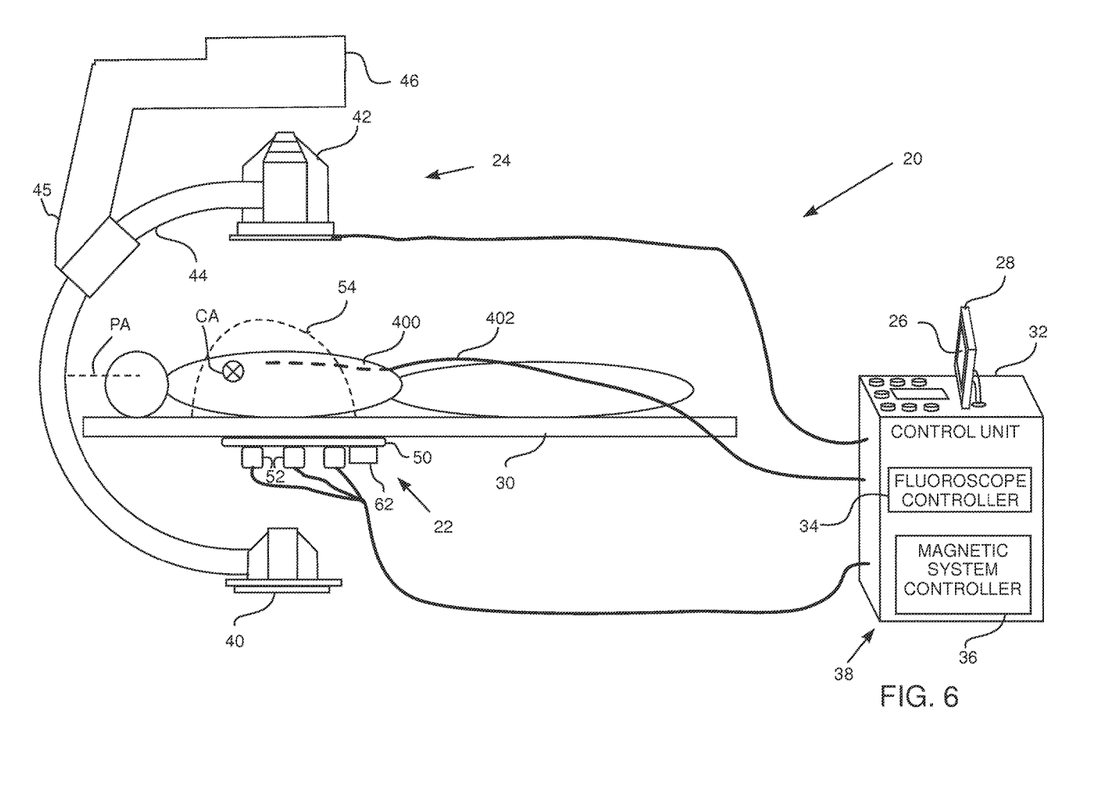
FIG. 6 is a schematic diagram illustrating the system of FIG. 1 in an operational phase, according to an embodiment of the present invention.

FIG. 6 is a schematic diagram illustrating system 20 in an operational phase, according to an embodiment of the present invention. Apart from the differences described below, the operation of system 20 in its operational phase is generally similar to that of the system in its calibration phase, and elements indicated by the same reference numerals in both FIG. 1 and FIG. 6 are generally similar in construction and in operation.

During the operational phase, jig 60 is removed, a patient 400 is positioned on table 30, and a catheter 402 with a magnetic sensor is inserted into the patient so that the sensor is in region 54. By way of example, the patient is assumed to be positioned in a head first supine (HFS) orientation. Positioning the patient on the table may move the table, and its attached location pad 50 and registration module 62, from its calibration phase state, so that the magnetic coordinate system of the fields generated by the location pad may no longer be in the registration with the fluoroscope coordinate system achieved by the steps of flowchart 300. Other changes from the calibration phase may occur, such as movement of table 30, and/or movement of the location pad with respect to the table, so that the transformation $[T_1]$ generated in step 314 may no longer be correct.

Embodiments of the present invention use an image of registration module 62 to re-register the magnetic coordinate system with the fluoroscope coordinate system, as is described in more detail below with regard to a flowchart 500 of FIG. 7.

Figure 7:
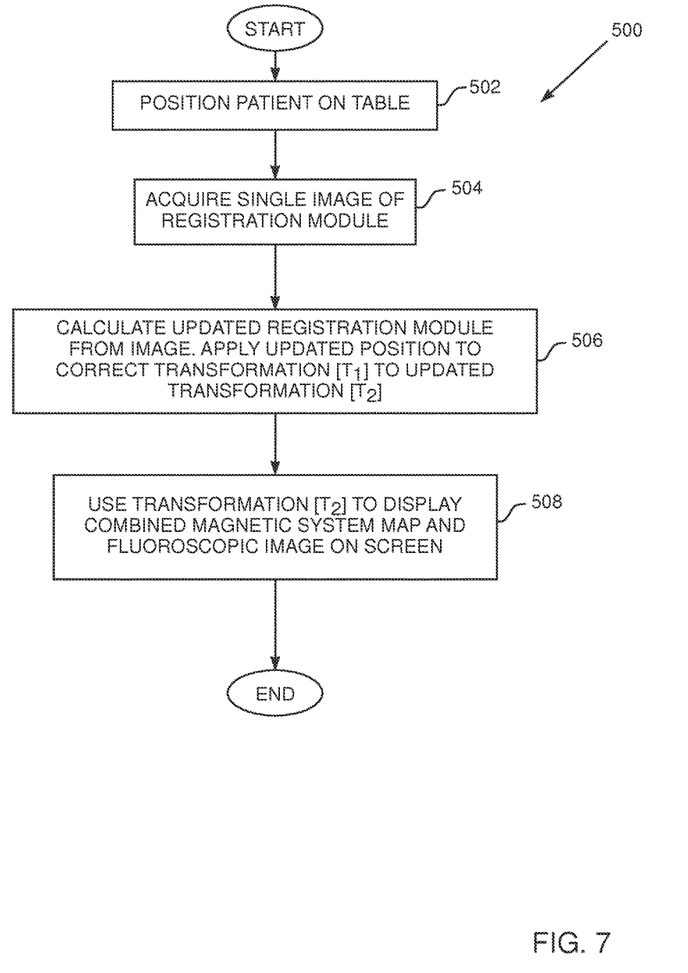
FIG. 7 shows a flowchart of steps for combining a magnetic tracking coordinate system map with a fluoroscope coordinate system image, according to an embodiment of the present invention.

FIG. 7 shows flowchart 500 of steps for combining a magnetic tracking coordinate system map with a fluoroscope coordinate system image, according to an embodiment of the present invention. In the description of flowchart 500, it is assumed that the steps of flowcharts 200 and 300 have already been performed. The steps of flowchart 500 correspond to the operational phase of system 20. In contrast to the calibration phase of the system, wherein no patient is present, in the operational phase a patient is present, so that X-ray exposure of the patient should be minimized.

In an initial step 502, patient 400 is positioned on table 30. As described above, positioning the patient on the table alters the physical position of the location pad from the position used in finding transformation $[T_1]$, so that the registration between the two systems has changed, and so that the transformation may no longer apply accurately.

To compensate for the change of location pad physical position, in an imaging step 504 a single image of the registration module is acquired by detector 42 in the fluoroscope system. While the position in the fluoroscope system of the registration module has changed, the position of the module within the magnetic coordinate system, as determined in step 314 of flowchart 300, has not changed, since the registration module is physically connected to the location pad. In other words, transformation $[T_{magnetic,module}]$ is still valid.

In a re-registration step 506 processor 38 uses the image acquired in step 504 to calculate an updated transformation between the fluoroscope system and the registration module: $[T_{module,fluoro,new}]$. The processor then applies the updated transformation, in order to calculate a transformation $[T_2]$ (which is an updated transformation $[T_1]$), according to equation (2):

$$[T_{module,fluoro,new}] * [T_{magnetic,module}] = [T_2] \quad (2)$$

Equation (2) is also applied, by finding new values of $[T_{module,fluoro,new}]$, for every movement of table 30 (causing the location pad to move). The new values are based on the table calibration results determined in table calibration step 206 of flowchart 200.

In a display generation step 508 processor 38 uses transformation $[T_2]$ to register elements having positions determined in the two systems, and to present the resultant combined image on screen 28 as an overlay of a fluoroscope coordinate system image on a magnetic coordinate system map. The method for combining the image and the map takes account of different methods typically used for generating the image and the map in each system, as described below with reference to FIG. 8. The method for combining the image with the map may typically also be dependent on the elements present in the image and the map.

Figure 8:
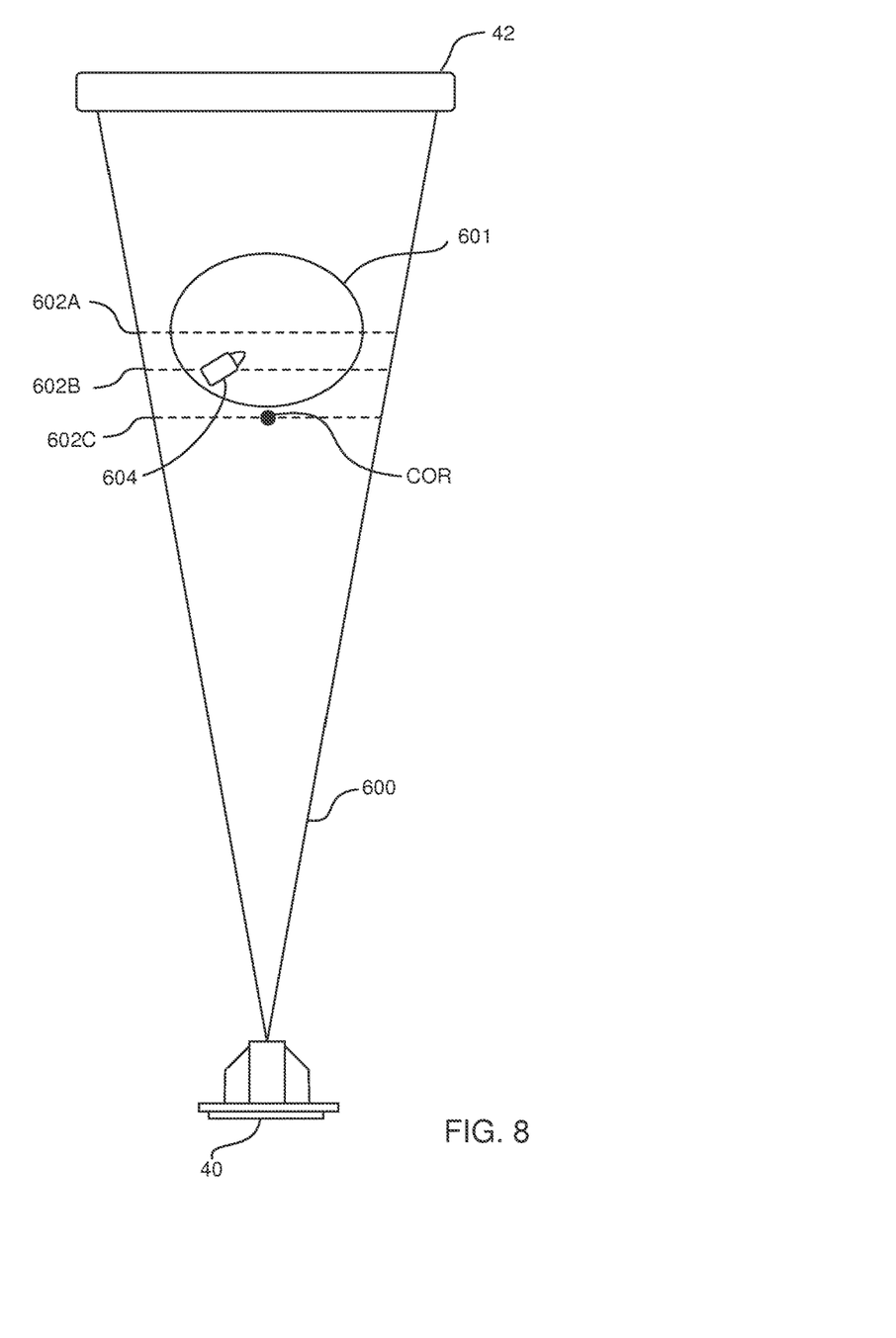
FIG. 8 is a schematic diagram illustrating methods for combining the image and the map of FIG. 7, according to an embodiment of the present invention.

FIG. 8 is a schematic diagram illustrating methods for combining the image and the map of FIG. 7, according to an embodiment of the present invention. Source 40 acts as a point source of X-rays, which radiate through a "pyramid" 600, so that in the fluoroscope system the 2D image acquired by detector 42 of a 3D volume of interest 601 in the pyramid corresponds to a perspective projection, where the source acts as the origin of the projection, and wherein projection lines (not shown on the diagram) radiate from the source to the detector. However, the 2D display of the 3D volume of interest, as presented in the magnetic system, is typically different from a perspective projection. For example, in the Carto system referred to above, wherein the volume of interest is the heart, a 3D electropotential map of the heart is typically provided on screen 28 as an orthographic projection, wherein projection lines through the heart are parallel to each other.

Embodiments of the present invention allow an operator of system 20 to select an effective "plane" 602, parallel to detector 42, within pyramid 600 which is to be used for aligning and positioning the perspective projection in the fluoroscope system with the orthographic projection in the magnetic system. The plane selected is a plane within the 3D volume of interest.

Three examples of the planes, assuming that the volume of interest corresponds to a heart electropotential map, are shown in the figure, although other planes may be used. A plane 602A is a plane through a center of gravity of the electropotential map; a plane 602B is a plane through an item of interest 604 in the map; and a plane 602C is a plane through a center of rotation COR of the fluoroscope system, as projected onto the map. Selection of the different planes is effected by deciding on a point in the image and in the map that is to correspond, and then adjusting a magnification of the perspective projection.

The magnetic system typically determines both the location and orientation of catheters that are tracked by the system. Thus, for example, if item of interest 604 corresponds to the distal tip of a catheter, an icon of the catheter may be used in the combined display presented on screen 28, and the icon image may be varied to represent both the location and orientation of the catheter.

The description above has assumed that the perspective projection of the fluoroscope system is incorporated into the orthographic projection of the magnetic system. However, the description may be applied, mutatis mutandis, to converting the orthographic projection of the magnetic system into a perspective projection. The perspective projection of the fluoroscope system may then be incorporated into the magnetic perspective projection.

Returning to image generation step 508 (FIG. 7), once transformation $[T_2]$ has been formulated, the transformation may be applied for substantially any display on screen 28 that is desired by the system operator. Furthermore, the transformation may be applied completely automatically for the chosen display, and may be applied to real-time imaging as well as to stored images.

Typically, processor 38 may import and store every image generated by the fluoroscope. The processor may then process the fluoroscopic image to derive the desired image plane coordinates (in the magnetic system), and store the image along with these coordinates. This image can then be viewed aligned and in overlay with the magnetic system map.

Similarly, when the operator rotates the magnetic system map to see a different view, and this view angle corresponds to a projection angle at which a fluoroscopic image was previously captured and stored, the processor may recall the corresponding image automatically and display it together with the map. Alternatively or additionally, if no fluoroscopic image has been acquired and stored at the current map viewing angle, processor 38 may automatically instruct the fluoroscope to acquire an image for display together with the magnetic system map at this angle.

As a further option, the operator can set the magnetic mapping system so that upon acquiring a fluoroscopic image at a certain angle (or displaying a previously-acquired image), processor 38 automatically rotates the magnetic system map so that the projection angle of the map matches that of the fluoroscopic image. This technique ensures that the magnetic system map projection and the fluoroscopic projection that are displayed at any time are in proper registration and helps to prevent operator errors in carrying out the procedure.

The technique described above can be used not only to import and register entire fluoroscopic images into the magnetic mapping system, but also to import and register particular objects—such as particular anatomical structures and features—that may be segmented in a fluoroscopic image. Based on registration of the fluoroscopic image from which the object is taken, each such object will have a location and orientation in the magnetic coordinate system. An object selected by the user can thus be registered and superimposed on the magnetic map with little or no user involvement in the actual registration process.

The processor can also invert the fluoroscopic image by 180°. For example, when the fluoroscopic image is taken in HFS view, and the orientation of the magnetic system map is also HFS, the fluoroscopic image may be displayed on the magnetic system map. If the magnetic system map orientation is inverted, on the other hand, the processor can invert the fluoroscopic image from the HFS view, and thus continue to display the fluoroscopic image in proper registration with the magnetic system image. In treating atrial fibrillation, for example, the operator usually sets the magnetic system orientation inverted from the HFS view, in order to see the veins while ablating. With the inverted view, the operator will also be able to see also the fluoroscopic image in the inverted view, even when the fluoroscope itself is unable to actually capture images in this orientation.

The ability of the system to register fluoroscopic images with the magnetic system map, and to present correctly the appropriate fluoroscopic image at each angle of projection of the magnetic system map, can be used in various other ways to enhance visualization during catheterization procedures. For example, the magnetic system map may be rotated and corresponding fluoroscopic images may be displayed in order to enable the operator to verify the distance between the arteries and the catheter tip.

Fluoroscopic images that have been registered with the magnetic system map can also be used to assist in aligning and registering other images, such as CT (computerized tomography) or MRI (magnetic resonance imaging) images, with the magnetic system map.

Registration of fluoroscopic images with magnetic maps in the manner described above can be useful in reducing the X-Ray dosage to which patients are exposed. For example, the operator may be able to carry out catheter insertion without simultaneous X-Ray imaging by using pre-acquired, registered fluoroscopic images. Similarly, a pair of pre-acquired, registered fluoroscopic images from different angles can be used to assist the operator in inserting a catheter at a certain location (such as the coronary sinus) based on the magnetic map without requiring simultaneous X-Ray imaging. Fluoroscopic cine loops can also be registered in the manner described above and then played back in proper registration during magnetic mapping and treatment.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. An apparatus for generating a transformation between a magnetic coordinate system and a fluoroscopic coordinating system, said apparatus including:
    a magnetic tracking coordinate system;
    a magnetic system controller;
    a fluoroscope;
    a fluoroscope coordinate system;
    a fluoroscope controller;
    a patient table;
    a location pad attached to the patient table;
    coils attached to the location pad for transmitting magnetic fields under control of the magnetic system controller;
    a coordinate system calibration jig; and
    a plurality of spheres on the coordinate system calibration jig for providing a fluoroscopic image of the spheres whereby the fluoroscopic controller analyzes the fluoroscopic image to determine a location and an orientation of the coordinate system calibration jig in the fluoroscopic coordinate system;
    a number of magnetic sensors attached to the coordinate system calibration jig whereby signals from the magnetic sensors generated in response to the transmitted magnetic fields from the location pad coils are analyzed by the magnetic system controller to determine a location and an orientation of the coordinate system calibration jig in the magnetic coordinate system;
    a registration module comprising radiopaque elements arranged in a fixed predetermined pattern in fixed connection to the location pad and configured in response to the radiopaque elements being imaged by the fluoroscope to enable the fluoroscopic controller to generate a position of the registration module in the fluoroscopic coordinate system; and
    a system processor which receives the results of the location and orientation of the coordinate system calibration jig in the fluoroscopic coordinate system and in the magnetic coordinate system as well as the registration module in the fluoroscopic coordinate system to generate a transformation between the fluoroscopic coordinate system and the magnetic coordinate system.

2. An apparatus according to claim 1 wherein the plurality of spheres on the coordinate system calibration jig are metal.

3. An apparatus according to claim 1 including one or more connections configured to connect the registration module to the location pad at a predetermined location and orientation with respect to the location pad, so as to characterize the position of the registration module in the magnetic coordinate system.

4. An apparatus according to claim 1 wherein the registration module comprises a pair of parallel plates defining a line of symmetry and wherein the radiopaque elements comprise a plurality of radiopaque markers distributed symmetrically above the line.

5. An apparatus according to claim 1 wherein the registration module comprises a pair of parallel plates defining a line of symmetry, and wherein the radiopaque markers are distributed symmetrically about the line.

6. An apparatus according to claim 1 wherein the predetermined shape is selected from a group containing a disk and a rectangle.

7. The apparatus according to claim 1 wherein the spheres are spaced evenly within a period of a helical pattern.

8. The apparatus according to claim 7 wherein each period of the helical pattern comprises a different number of radio opaque elements.

9. The apparatus according to claim 7 wherein at least some of the periods of the helical pattern have different lengths as compared to other periods of the helical pattern, and wherein the periods of the helical patterns are spaced unevenly.

10. The apparatus according to claim 1 further comprising a catheter having one or more coils, the coils being adapted to generate signals in response to magnetic fields generated by coils of the magnetic tracking system.

11. The apparatus according to claim 1 wherein the coordinate system calibration jig includes retro-reflectors having openings for receiving removable balls.

12. The apparatus according to claim 11 wherein the retro reflectors comprise a plurality of cavities in the exterior surface of the coordinate system calibration jig, and a plurality of removable balls each positioned in one of said plurality of cavities.

13. The apparatus according to claim 1 wherein the coordinate system calibration jig further comprises a catheter holder shaped to temporarily hold a catheter.

14. The apparatus according to claim 1 wherein the plurality of spheres are arranged in one or more straight lines along an exterior surface of the coordinate system calibration jig and wherein at least some of the spheres are not identical to other spheres which are arranged in the helical pattern.

15. The apparatus according to claim 1 wherein the plurality of spheres are arranged in each of two or more straight lines along an exterior surface of the coordinate system calibration jig, the straight lines being parallel to the center axis of the jig body; and wherein at least some of the spheres are not identical to the spheres which are arranged in the helical pattern.

* * * * *